US00PP09440P

United States Patent [19]

VandenBerg

[11] Patent Number: Plant 9,440

[45] Date of Patent: Jan. 23, 1996

[54] CHRYSANTHEMUM PLANT NAMED 'HEATHER'

[75] Inventor: Cornelis P. VandenBerg, Salinas, Calif.

[73] Assignee: Yoder Brothers Inc., Barberton, Ohio

[21] Appl. No.: 366,498

[22] Filed: Dec. 30, 1994

[51] Int. Cl.[6] ..... A01H 5/00

[52] U.S. Cl. ..... Plt./76

[58] Field of Search ..... Plt./76

*Primary Examiner*—Howard J. Locker
*Attorney, Agent, or Firm*—Foley & Lardner

[57] ABSTRACT

A Chrysanthemum plant named Heather particularly characterized by its flat capitulum form; decorative capitulum type; red-purple ray floret color; diameter across face of capitulum of 48 to 54 mm when fully opened; branching pattern is spreading and prolific; natural season flower date of September 2 to 5 when planting rooted cuttings on June 21 to 25 in Salinas, Calif., and September 30 to October 3 when planting rooted cuttings June 15 to June 21 in Hightstown, N.J.; plant height of 23 to 33 cm when grown in fall under natural daylength with no growth regulators in Salinas, Calif., and 30 to 36 cm when grown in fall under natural daylength with no growth regulator applications in Hightstown, N.J.; excellent, uniform growth habit; and good flexibility of plant for handling, packing and shipping.

3 Drawing Sheets

The present invention comprises a new and distinct cultivar of Chrysanthemum, botanically known as *Dendranthema grandiflora,* and referred to by the cultivar name Heather.

Heather, identified as 8868 (90-876005), was originated from a cross made by Cornelis P. VandenBerg in a controlled breeding program in Salinas, Calif., in April 1990.

The female parent of Heather was the cultivar identified as Debonair, disclosed in U.S. Plant Pat. No. 5,324.

The male parent of Heather was an unnamed seedling, identified as 8882 (87-289003) and described as a pink-purple decorative garden mum with many disc florets.

Heather was discovered and selected as one flowering plant within the progeny of the stated cross by Cornelis P. VandenBerg in January 1991, in a controlled environment in Salinas, Calif.

The first act of asexual reproduction of Heather was accomplished when vegetative cuttings were taken from the initial selection in April 1991 in a controlled environment in Salinas, Calif., by technicians working under supervision of Cornelis P. VandenBerg.

Horticultural examination of controlled flowerings of successive plantings has shown that the unique combination of characterisitcs as herein disclosed for Heather are firmly fixed and are retained through successive generations of asexual reproduction.

Heather has not been observed under all possible environmental conditions. The phenotype may vary significantly with variations in environment such as temperature, light intensity and daylength, without, however, any variance in genotype.

The following observations, measurements and comparisons describe plants grown in controlled open areas in Hightstown, N.J. Rooted cuttings were established in soil and maintained outdoors under the natural temperature and daylength prevailing during June through October.

The following traits have been repeatedly observed and are determined to be basic characteristics of Heather, which, in combination, distinguish this Chrysanthemum as a new and distinct cultivar:

1. Flat capitulum form.
2. Decorative capitulum type.
3. Red-purple ray floret color.
4. Diameter across face of capitulum of 48 to 54 mm when fully opened.
5. Branching pattern is spreading and prolific.
6. Natural season flower date of September 2 to 5 when planting rooted cuttings on June 21 to 25 in Salinas, Calif., and of September 30 to October 3 when planting rooted cuttings June 15 to June 21 in Hightstown, N.J.
7. Plant height of 23 to 33 cm when grown in fall under natural daylength with no growth regulators in Salinas, Calif., and of 30 to 36 cm when grown in fall under natural daylength with no growth regulator applications in Hightstown, N.J.
8. Excellent, uniform growth habit.
9. Good flexibility of plant for handling, packing and shipping.

The accompanying photographic drawings show typical inflorescence and leaf characteristics of Heather, with the colors being as nearly true as possible with illustrations of this type.

Sheet 1 is a color photograph of Heather grown outside in Salinas, Calif., and dug and transplanted into a 15 cm pot at flowering time for photography purposes.

Sheet 2 is a black and white photograph of three views of the inflorescence of Heather.

Sheet 3 is a black and white photograph showing the upper and under sides of the leaves of Heather at three stages of development (mature, intermediate and immature). In sheets 2 and 3 a measuring tape in centimeters has been added.

Of the commercial cultivars known to the inventor, the most similar in comparison to Heather is the female parent Debonair. Reference is made to attached Chart A, which compares certain characteristics of Heather to the same characteristics of Debonair.

Similar traits are capitulum form and type and comparable plant height. The ray floret color of Heather is red-purple, while the ray floret color of Debonair is purple. Heather has a smaller diameter of capitulum, a more spreading plant habit, and a slower natural season flowering date than Debonair in both Salinas, Calif. and in Hightstown, N.J.

In the following description, color references are made to The Royal Horticultural Society Colour Chart. The color values were determined on plant material grown as a pinched garden mum grown outdoors in Salinas, Calif. on Aug. 21, 1994.

Classification:

*Botanical.*—*Dendranthema grandiflora,* cv., Heather.

*Commercial.*—Flat decorative garden mum.

INFLORESCENCE

Capitulum:

*Form.*—Flat.

*Type.*—Daisy.

*Diameter across face.*—48 to 54 mm when fully opened.

Corolla of ray flroets:

*Color (general tonality from a distance of three meters).*—Red-purple.

*Color (upper surface).*—70A to 70B, maturing to between 70B and 70C.

*Color (under surface).*—75B, overlaid with 71B.

*Shape.*—Cross section of florets concave, ribbed; longitudinal section of outer ray florets straight.

Corolla of disc florets:

*Color (mature).*—7A.

*Color (immature).*—144C.

Reproductive organs:

*Androecium.*—Present on disc florets only; scant to no pollen.

*Gynoecium.*—Present on both ray and disc florets.

PLANT

General appearance:

*Height.*—23 to 33 cm when grown in fall under natural daylength with no growth regulators in Salinas, Calif., and 30 to 36 cm when grown in fall under natural daylength with no growth regulator applications in Hightstown, N.J.

*Branching pattern.*—Spreading and prolific.

Foliage:

*Color (upper surface).*—147A.

*Color (under surface).*—147B.

*Shape.*—Very deeply lobed, serrated.

CHART A
COMPARISONS MADE OF PLANTS GROWN UNDER NATURAL SEASON OUTDOOR CONDITIONS IN SALINAS, CALIFORNIA AND HIGHTSTOWN, NEW JERSEY

| | HEATHER | DEBONAIR |
|---|---|---|
| Ray floret color | Red-purple | Purple |
| Capitulum form and type | Flat, decorative | Flat, decorative |
| Diameter across face of capitulum | 48 to 54 mm | 64 to 70 mm |
| Branching pattern | Spreading and prolific | Spreading |
| Natural season flower date | | |
| in Salinas, CA | Sept. 2 to 5 | Aug. 26 to 31 |
| Hightstown, NJ | Sept. 30 to Oct. 3 | Sept. 24 to 30 |
| Plant height in natural season fall: | | |
| in Salinas, CA | 23 to 33 cm | 23 to 30 cm |
| in Hightstown, NJ | 30 to 36 cm | 30 to 38 cm |

It is claimed:

1. A new and distinct Chrysanthemum plant named Heather, as described and illustrated.

* * * * *

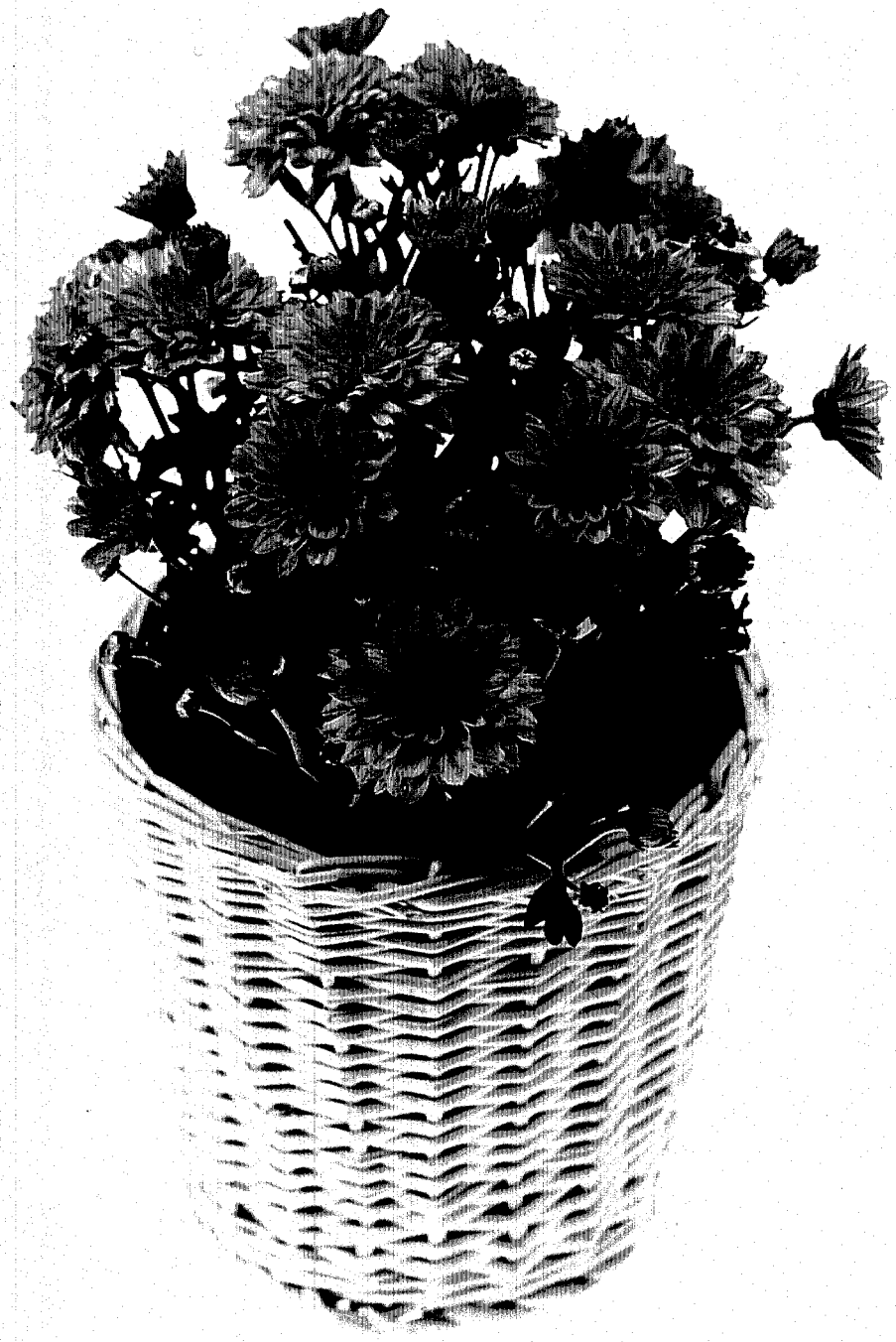

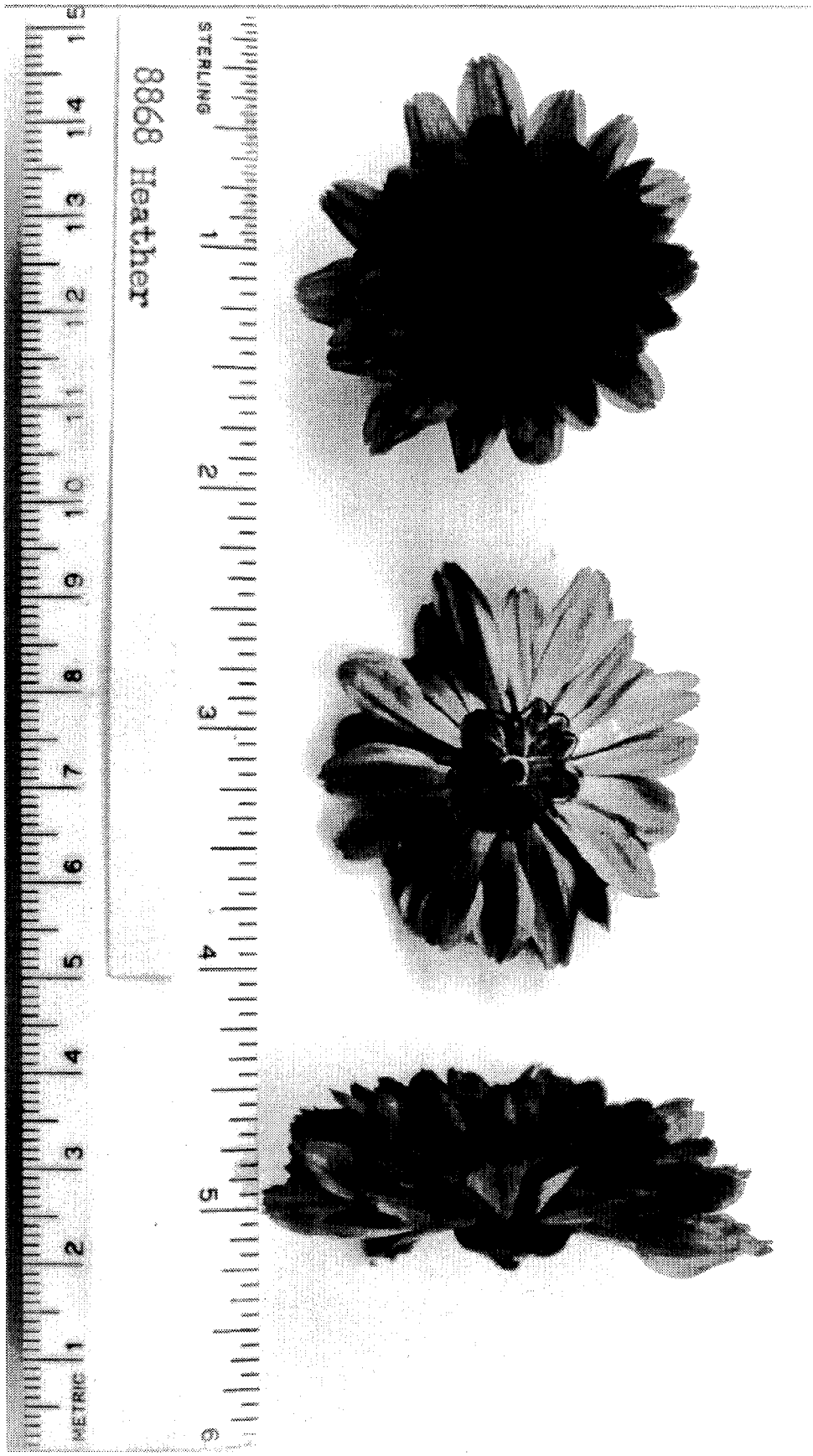
8868 Heather
STERLING
METRIC

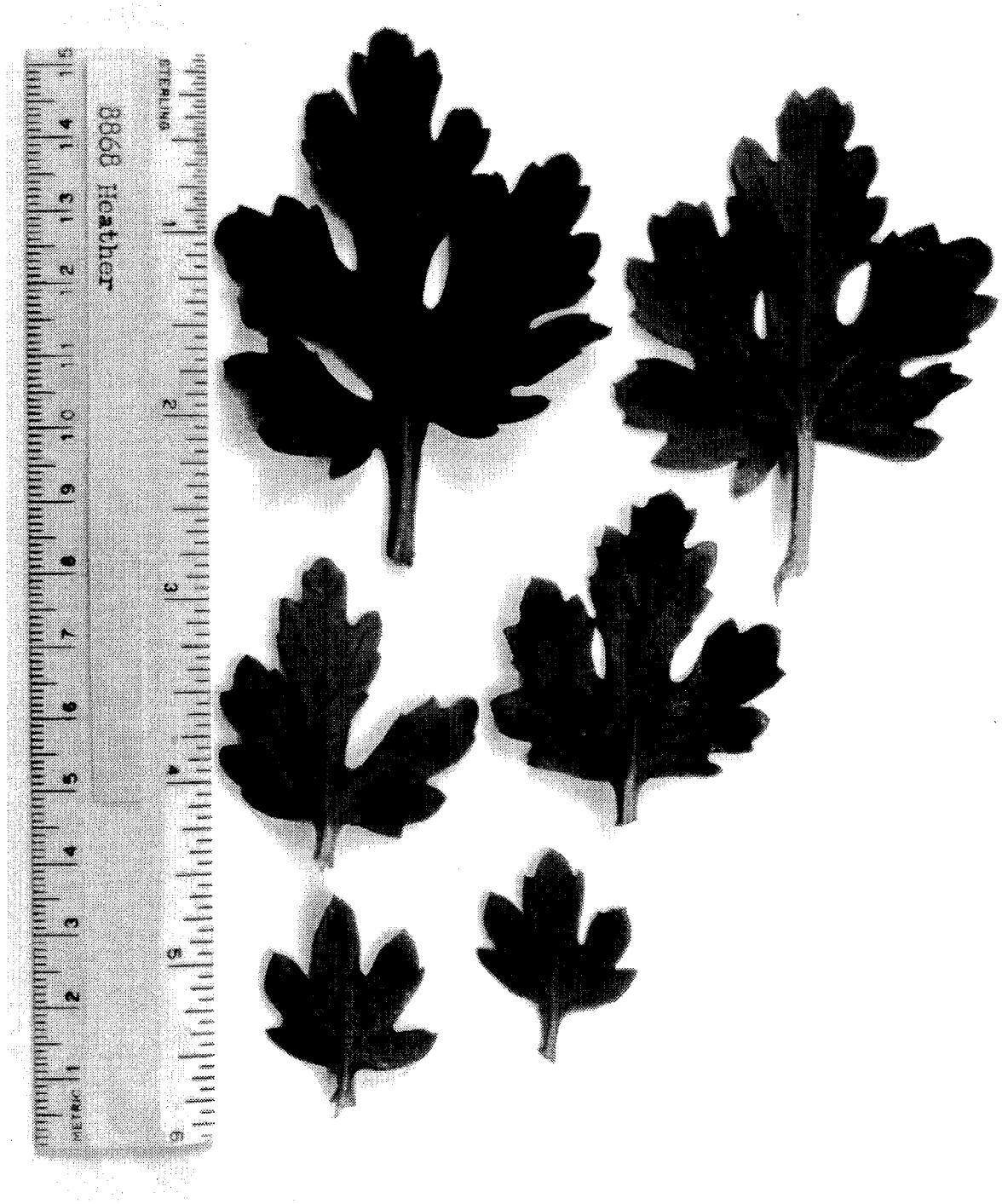
8868 Heather